United States Patent
Abrams et al.

(10) Patent No.: US 7,343,914 B2
(45) Date of Patent: Mar. 18, 2008

(54) ADAPTORS FOR INHALERS TO IMPROVE PERFORMANCE

(75) Inventors: Andrew L. Abrams, Westport, CT (US); Anand V. Gumaste, Princeton Junction, NJ (US)

(73) Assignee: Microdose Technologies, Inc., Monmouth Junction, NJ (US)

( * ) Notice: Subject to any disclaimer, the term of this patent is extended or adjusted under 35 U.S.C. 154(b) by 162 days.

(21) Appl. No.: 10/236,155

(22) Filed: Sep. 6, 2002

(65) Prior Publication Data

US 2003/0041859 A1  Mar. 6, 2003

Related U.S. Application Data

(60) Provisional application No. 60/317,706, filed on Sep. 6, 2001.

(51) Int. Cl.
*A61M 11/00* (2006.01)
*A61M 15/00* (2006.01)

(52) U.S. Cl. .............. 128/200.23; 128/203.15
(58) Field of Classification Search ........... 128/200.12, 128/200.14, 200.17, 200.18, 200.22, 200.23, 128/203.12, 203.15, 203.18, 203.19, 203.21, 128/204.25, 202.27, 201.26, 201.11; 604/58
See application file for complete search history.

(56) References Cited

U.S. PATENT DOCUMENTS

| | | | | |
|---|---|---|---|---|
| 2,865,370 A | * | 12/1958 | Gattone | 128/200.23 |
| 4,240,418 A | * | 12/1980 | Rosskamp et al. | 128/203.15 |
| 4,470,412 A | | 9/1984 | Nowacki et al. | |
| 4,581,013 A | * | 4/1986 | Allen | 604/78 |
| 4,792,333 A | * | 12/1988 | Kidder | 604/83 |
| 4,832,015 A | | 5/1989 | Nowacki et al. | |
| 5,020,527 A | | 6/1991 | Dessertine | |
| 5,042,467 A | * | 8/1991 | Foley | 128/200.23 |
| 5,284,133 A | | 2/1994 | Burns et al. | |
| 5,363,842 A | | 11/1994 | Mishelevich et al. | |
| 5,477,849 A | * | 12/1995 | Fry | 128/200.14 |
| 5,482,030 A | | 1/1996 | Klein | |
| 5,497,765 A | * | 3/1996 | Praud et al. | 128/200.23 |
| 5,505,195 A | * | 4/1996 | Wolf et al. | 128/203.15 |
| 5,522,380 A | * | 6/1996 | Dwork | 128/200.23 |
| 5,535,741 A | | 7/1996 | Widerstrom et al. | |
| 5,673,686 A | * | 10/1997 | Villax et al. | 128/203.15 |
| 5,676,130 A | * | 10/1997 | Gupte et al. | 128/203.19 |
| 5,746,197 A | * | 5/1998 | Williams | 128/200.23 |
| 5,778,873 A | | 7/1998 | Braithwaite | |
| 5,794,612 A | * | 8/1998 | Wachter et al. | 128/200.23 |
| 5,797,392 A | * | 8/1998 | Keldmann et al. | 128/203.15 |
| 5,809,996 A | * | 9/1998 | Alldredge | 128/200.23 |
| 5,839,430 A | | 11/1998 | Cama | 128/200.14 |
| 5,848,588 A | * | 12/1998 | Foley et al. | 128/200.23 |
| 5,855,202 A | * | 1/1999 | Andrade | 128/200.14 |
| 5,924,417 A | | 7/1999 | Braithwaite | |
| D412,979 S | * | 8/1999 | Weinstein et al. | D24/110 |

(Continued)

FOREIGN PATENT DOCUMENTS

EP  0 667 168  2/1994

(Continued)

*Primary Examiner*—Teena Mitchell
(74) *Attorney, Agent, or Firm*—Hayes Soloway P.C.

(57) ABSTRACT

A child-sized adaptor for a DPI or MDI is provided. Also provided is a patient feedback mechanism for signaling and/or teaching proper inhaler use.

48 Claims, 6 Drawing Sheets

U.S. PATENT DOCUMENTS

| | | | | |
|---|---|---|---|---|
| 6,014,972 A | * | 1/2000 | Sladek | 128/203.12 |
| 6,026,808 A | * | 2/2000 | Armer et al. | 128/200.23 |
| 6,085,742 A | * | 7/2000 | Wachter et al. | 128/200.23 |
| 6,138,673 A | * | 10/2000 | Shepherd | 128/203.15 |
| 6,142,146 A | | 11/2000 | Abrams et al. | |
| 6,158,676 A | | 12/2000 | Hughes | 239/405 |
| 6,202,642 B1 | * | 3/2001 | McKinnon et al. | 128/200.23 |
| 6,202,643 B1 | * | 3/2001 | Sladek | 128/200.23 |
| 6,230,704 B1 | * | 5/2001 | Durkin et al. | 128/200.22 |
| 6,240,917 B1 | * | 6/2001 | Andrade | 128/200.23 |
| 6,257,231 B1 | * | 7/2001 | Shick et al. | 128/200.14 |
| 6,333,050 B2 | * | 12/2001 | Wong et al. | 424/473 |
| 6,347,629 B1 | * | 2/2002 | Braithwaite | 128/203.15 |
| 6,390,088 B1 | * | 5/2002 | Nohl et al. | 128/200.23 |
| 6,394,085 B1 | * | 5/2002 | Hardy et al. | 128/203.15 |
| 6,425,392 B1 | * | 7/2002 | Sosiak | 128/200.23 |
| 6,470,882 B1 | * | 10/2002 | Newhouse et al. | 128/200.24 |
| 2003/0101991 A1 | * | 6/2003 | Trueba | 128/200.14 |
| 2003/0205229 A1 | * | 11/2003 | Crockford et al. | 128/204.23 |

FOREIGN PATENT DOCUMENTS

| | | |
|---|---|---|
| EP | 0933092 | 4/1999 |
| EP | 0667168 B1 | 6/2000 |
| GB | 2 294 402 | 5/1996 |
| RU | 2071789 C * | 1/1997 |
| WO | WO 97/18003 | 5/1997 |
| WO | WO 99/53982 | 10/1999 |
| WO | WO 99/64095 | 12/1999 |
| WO | WO 01/19436 | 3/2001 |

* cited by examiner

ADAPTORS FOR INHALERS TO IMPROVE PERFORMANCE

CROSS-REFERENCE TO RELATED APPLICATION

This Application claims priority from U.S. Provisional Application Ser. No. 60/317,706 filed Sep. 6, 2001.

BACKGROUND OF THE INVENTION

The present invention relates generally to the field of inhalation devices, and more specifically, to a mouthpiece adaptor and patient feedback for an inhaler. The invention has particular utility as a mouthpiece adaptor and patient feedback for inhalation devices such as dry powder inhalers ("DPIs") for facilitating use of same by pediatric, geriatric and compromised patients, and will be described in connection with such utility, although other utilities are contemplated such as for use with metered dose inhalers ("MDIs") and nebulizers.

Metered dose inhalers (MDIs) depend on delivery technique to deliver the proper amount of medication to the lungs. A properly delivered MDI medication depends on dexterity, coordination, timing, and practice. This can be a real problem when the patient is young, has coordination problems, or especially irritable airways.

An alternative to MDIs are dry powder inhaler devices (DPIs), which are activated by the patient's inspiratory effort, so that coordination is not a problem, although inhalation technique is still important. The drug is aerosolized by the airflow through a DPI created by the patient inhaling. DPI devices are easy to use and are thus suitable for most ages. Newer multidose types of powder devices have electronics which include dose counters, which enable patients to check whether or not they have taken a dose and warns them when the inhaler is running out of doses by showing them exactly how many doses remain. U.S. Pat. No. 6,142,146 to Abrams et al. discloses this type of device. However, dry powder inhalers require patients to inspire reasonably rapidly to inhale the dry powder, so these devices are not suitable for younger children and infants. Further, even if young children and infants could conform to the protocol for using the device, current devices have mouthpieces which are too cumbersome for these patients.

When dealing with bronchial diseases among children and infants, it is difficult to make the patient properly inhale the therapeutic substances necessary for treatment. When asthma makes its debut among infants and young children, typically at 8 months to 2.5 years, it is especially difficult to make a child or infant inhale the prescribed medical substances in the proper way. Children and infants have limited lung capacity and the force of a child's or infant's breath during inhalation (inhalation flow) is thus limited. This is even more apparent when the child or infant is suffering from asthma or other bronchial diseases. Parents also desire that the devices used for inhalation be as flexible as possible, as it is difficult to position the inhaler in a way that will allow proper inhalation by an infant.

For patients of limited or compromised inhalation capacity, inhalation therapy may be accomplished through the use of inhalation chambers. An inhalation chamber typically includes an inlet and fixture for a medicament dispenser, e.g., an MDI, and an expanded hollow body, which in the technical field of inhalers normally is called a "spacer" or inhalation chamber, having an outlet provided at the end remote from the inlet. An inhalation/exhalation valve, e.g., a one-way valve, typically is provided adjacent the outlet, and a mouthpiece is provided at the outlet. When such a device is used by older children or adults the mouthpiece is inserted between the teeth and the lips are closed around the mouthpiece. It is, however, not possible for young children and infants to hold such a mouthpiece between their lips. Moreover, these devices are constructed to be used by older children who have large lung capacity and who can inhale more forcefully. The inhalation/exhalation valves provided typically require a certain inhalation flow, which a child or infant is unable to generate, to open properly. Therefore, for satisfactory inhalation to be achieved by young children and infants, inhalation devices often are provided with a face mask.

However, some small children and infants find standard inhalation devices employing masks frightening, and, as a consequence, resist using them. Faced with strong resistance from children, many care-givers responsible for administering medication to children report a reluctance to offer air-borne drugs for use with standard inhalation devices employing masks on a regular basis. In addition, care-givers also report that even when attempted, the delivery of aerosol/gas medication to children is often sub-optimal because the child cries and/or forcibly removes the mask from their face before the medication is taken properly.

Many patients who cannot use MDIs or DPIs, even with inhalation chambers, are forced to use nebulizers. Nebulizers produce a cloud of medication by passing a jet of compressed air through a solution of a drug (jet nebulizers) or by dropping the drug solution onto a plate vibrating at high frequency (ultrasonic nebulizers). Nebulizers have the advantage of being able to be used by patients of all ages, including young babies, because coordination is unimportant. However, disadvantages of nebulizers include that they are cumbersome, expensive (both the machine and the drugs) and noisy; require a power source, typically lines (AC) current; treatment takes a long time, often around ten minutes; and young patients are required to wear a mask. The amount of drug delivered to the lungs is highly dependant on the breathing pattern of the patient. All these factors tie down the patient and care-giver.

Because nebulizers have the above problems, several devices have been developed in order to entice or teach children how to use MDIs or DPIs, so that a nebulizer is unnecessary. But, those devices designed for use by young children require a mask adaptor for the MDI or DPI. PCT Application No. 995398 to Watt and European Patent 667168 to Minar et al. disclose incentive systems of this type.

Quite apart from the foregoing, conventional MDIs and DPIs (and also inhalation chambers therefor) have mouthpieces sized for the adult population. Thus, conventional MDIs, DPIs and inhalation chambers therefor have mouthpieces that are too big to be comfortably used by small children and infants. Moreover, the mouthpieces of conventional MDIs, DPIs and spacers are primarily rectangular in shape, which is somewhat awkward, or at least unfamiliar, particularly to small children.

SUMMARY OF THE INVENTION

This invention seeks to solve the problems with the prior art by allowing young children, geriatric and compromised patients to use DPIs, MDIs and inhalation chambers maskfree. Another aspect of the invention seeks to solve the issue of consistent patient inhalation in the pediatric, geriatric or physically challenged patients. Another aspect of the invention seeks to solve the problem of patient compliance when the patient is young, thereby enabling them to use certain devices previously unavailable to them. Yet another aspect of the invention seeks to allow sick or infirm patients to receive a dosage of medicine through an extension to the mouthpiece, thereby allowing the patient to recline while receiving medicine through an inhaler.

DESCRIPTION OF DRAWINGS

Still other features and advantages of the present invention may be seen from the following detailed description taken in connection with the attached drawings wherein like numerals depict like parts, and wherein.

DETAILED DESCRIPTION OF THE PREFERRED EMBODIMENTS

The detailed description of the preferred embodiments illustrates the use of the adaptor with MDIs and DPIs. However, each of the described embodiments of the adaptor also can be used in conjunction with spacer devices and nebulizers.

Figure 1:
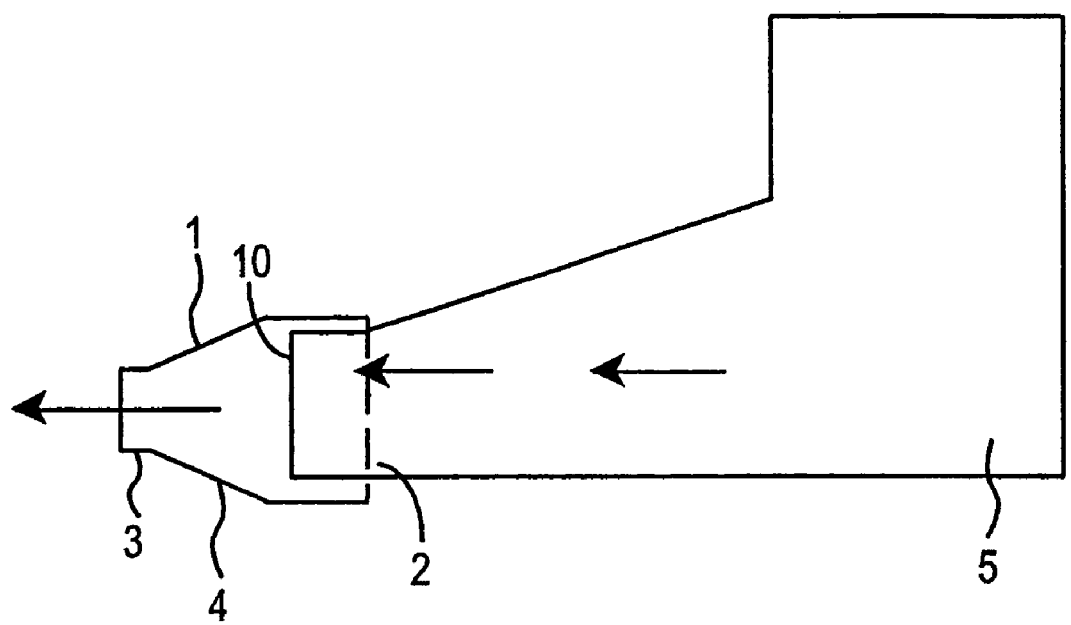
FIG. 1 is a longitudinal view of an exemplary adaptor for an inhaler attached to an inhaler according to one embodiment of the invention.
Figure 2:
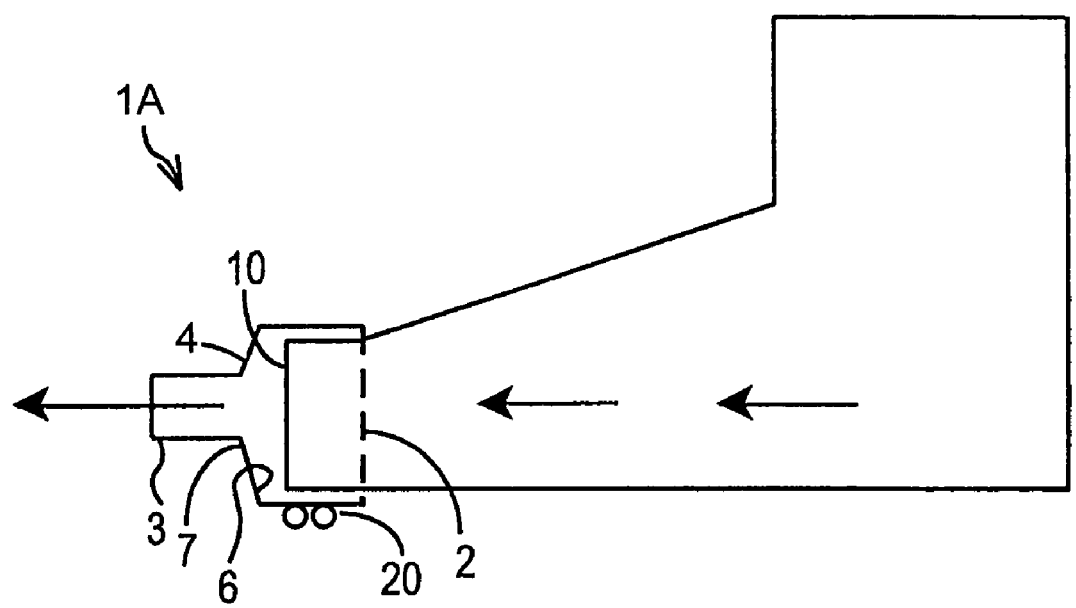
FIG. 2 is a longitudinal view of an exemplary adaptor for an inhaler attached to an inhaler according to another embodiment of the invention.

FIG. 1 illustrates one embodiment of an exemplary adaptor, wherein an adaptor 1 is attached to the mouthpiece 10 of an inhaler 5. The adaptor is attached to the inhaler mouthpiece 10 from a connecting side 2 using an attachment means that forms an airtight seal. In this embodiment, the adaptor side is designed to create a friction fit with the inhaler mouthpiece. The friction fit is accomplished by creating the connecting side 2 of the adaptor 1 to be just slightly larger in inside dimension than the outside dimension of the inhaler mouthpiece to which it is designed to attach, and sliding the adaptor onto the inhaler mouthpiece, thereby creating an airtight seal.

The adaptor 1 also includes a transition section 4 between a mouthpiece side 3 and an attachment side 2. The transition section 4 tapers the connecting side 2 of the adaptor to a child-sized mouthpiece side. Aerated particles enter and immediately pass through the connection means from the inhaler mouthpiece upon proper stimulation of the inhalation device. The connecting means does not act as a holding chamber. Here, the connection means is tapered in a funnel-like shape to minimize turbulence and prevent the coagulation of the aerated particles upon usage of the adaptor, which helps maintain the inhaler's effectiveness.

Figure 4:
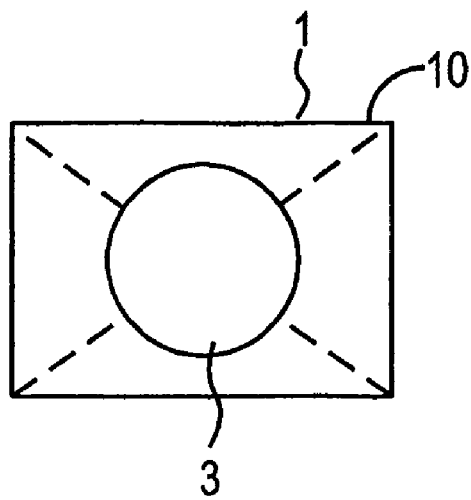
FIG. 4 is a frontal view of an exemplary adaptor for an inhaler and a mouthpiece for an adaptor according to one embodiment of the invention.
Figure 5:
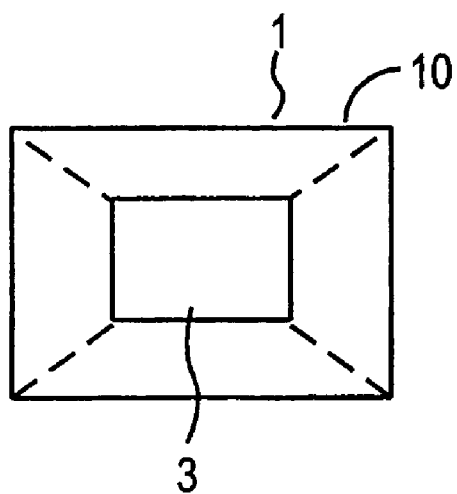
FIG. 5 is a frontal view of an exemplary adaptor for an inhaler and the mouthpiece of the adaptor according to another embodiment of the invention.

The mouthpiece side 3 is child-sized, similar in cross-sectional dimension to that of a drinking straw, i.e., having a diameter in the range of 1 mm to 15 mm, and is either round or oval shaped, as shown in FIG. 4. A round shape for the mouthpiece side is preferred for young children who are already familiar with this shape, i.e., from the use of drinking straws. That is to say, young children are already familiar with using a straw, and have shown that they are capable of proper inspirator pressures. Thus, the mouthpiece side straw-like size and shape not only encourages patient compliance, but also presents a familiar, less frightening alternative to a mask.

A second embodiment of the instant invention is shown in FIG. 2 as adaptor 1A. This embodiment, like the first, includes a connecting side 2, a transition section 4, and a mouthpiece side 3. As in the first embodiment, the connecting side 2 must facilitate the formation of an airtight seal. As shown in FIG. 2, this is accomplished by securing a plastic or metal clamp 20, which is located on the connecting side 2 of the adaptor 1A. Here, the connecting side 2 is larger in inside dimension than the outside dimension of the inhaler mouthpiece 10, and allows the adaptor to easily slide on the inhaler mouthpiece 10. Once the connecting side 2 of adaptor 1A is slid over the mouthpiece of the inhaler 10, the clamps 20 are fastened, creating the requisite airtight seal.

The mouthpiece adaptor of FIG. 2 includes a funnel-like region between the connecting side 2 and the mouthpiece side 3 comprising a slanted wall 7 formed opposite of the inhaler mouthpiece. A metal foil 6 is applied to the slanted wall connected to the circuit of the MDI or DPI and charged by the power source of the MDI or DPI, to the same charge as the particles. This causes a repulsion between the slanted wall and the particles whereby to prevent the particles from collecting on or colliding with the wall, and thus prevent coagulation of the particles on the interior adaptor walls. Further, as with the adaptor of FIG. 1, aerated particles only enter and pass through the adaptor of FIG. 2 upon proper stimulation of the inhalation device. i.e., the connection means does not act as a holding chamber.

The mouthpiece side of the adaptor of FIG. 2, as illustrated in FIG. 5, is manufactured as a replication of the inhaler mouthpiece. Like the mouthpiece side in the adaptor of FIG. 1, the mouthpiece side in the adaptor of FIG. 2 is child-sized, i.e., having cross-sectional dimensional area from 1 $mm^2$ to 200 $mm^2$. This design, like the round or cylindrical mouthpiece side, also has advantages. Because the shape of the mouthpiece side here is the shape of the inhaler mouthpiece, airflow is concentrated with minimum turbulence.

A third embodiment of the instant invention is shown in FIG. 3 as adaptor 1B. The third embodiment, like the first and second, includes a connecting side 2, a transition section 4, and a mouthpiece side 3. Here, the connecting side 2 is fitted to the inhaler mouthpiece 10 using an attachment means that employs a rubber ring to create an airtight seal. The connecting side 2 is slightly larger than the inhaler mouthpiece 10, and includes on the distal end a taut rubber ring 25 fitted over the connecting side 2. The connecting side 2 is slid over the mouthpiece 10, and the rubber ring is pushed from the top of adaptor connecting side 2 over the mouthpiece of the inhaler 10. In addition, the interior of the attachment side, in which the attachment side of an interior cone 9 is located, and the inhaler mouthpiece, link end to end, forming a seal. Thus, there is no ridge on which particles can coalesce, formed between the adaptor and the inhaler mouthpiece 10.

Figure 3:
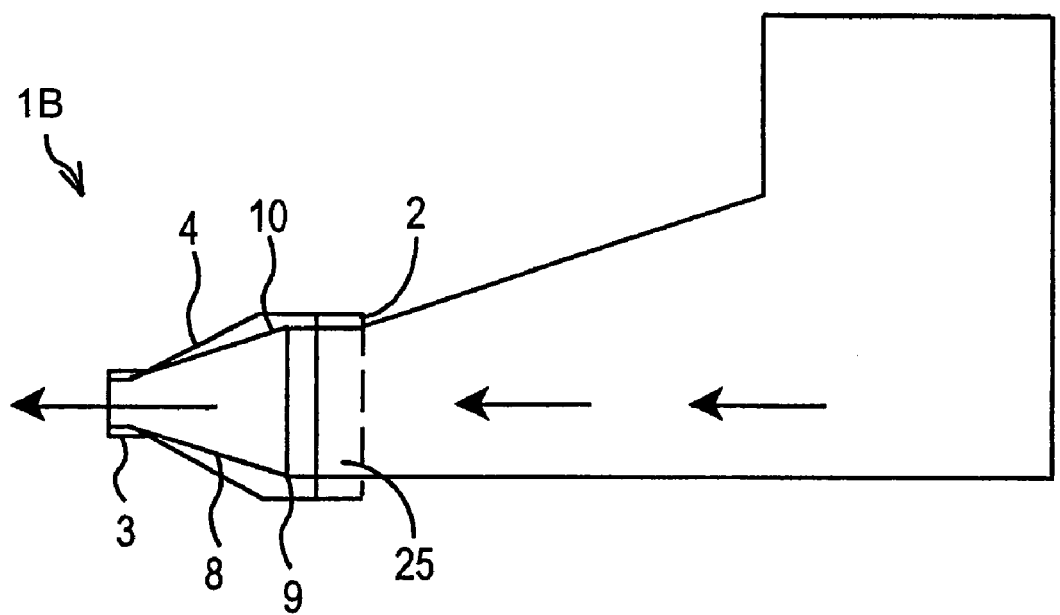
FIG. 3 is a longitudinal view of an exemplary adaptor for an inhaler attached to an inhaler according to yet another embodiment of the invention.

Further, in FIG. 3 a conical wall 8 is formed on the inside of the transition section 4. The interior wall forms a smooth transition between the inhaler mouthpiece and the adaptor, thereby allowing the particles to move through the inhaler mouthpiece with minimum turbulence. As in the above embodiments, aerated particles only enter and pass through the adaptor when the inhaler is stimulated to pass medication. Thus, the adaptor does not act to holdup flow of medication.

The mouthpiece side in the adaptor of FIG. 3 could be shaped, e.g., according to the first or second embodiment.

Figure 6:
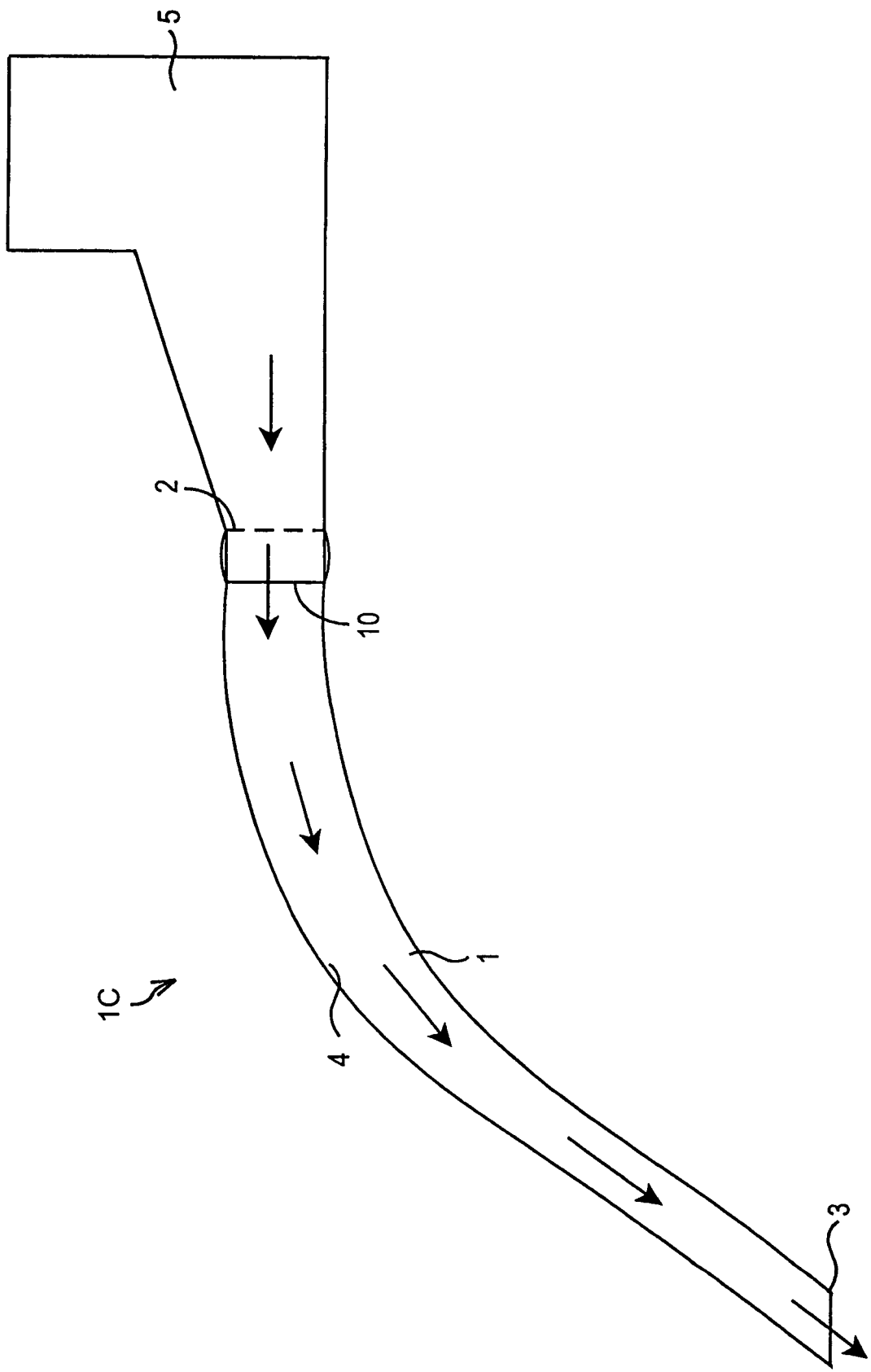
FIG. 6 is a longitudinal view of an exemplary adaptor for an inhaler attached to the inhaler according to yet another embodiment of the invention.
Figure 7:
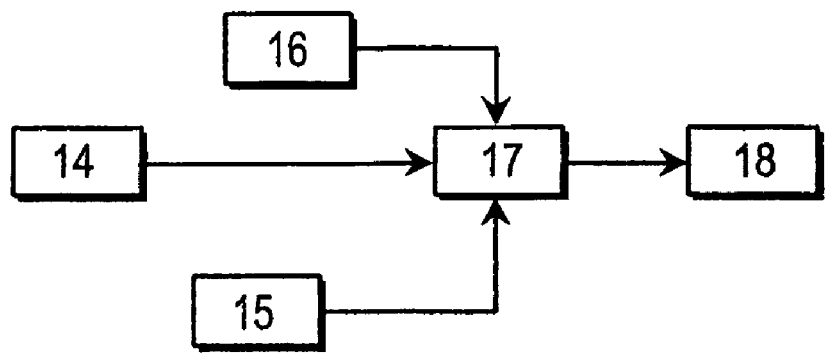
FIG. 7 is a functional block diagram of the sensor-light/sound mechanism of the invention according to one embodiment of the invention.
Figure 8:
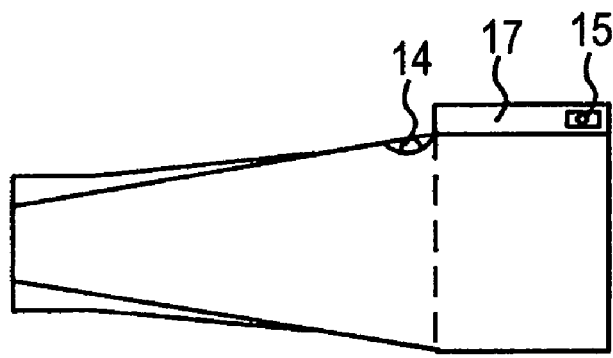
FIG. 8 is a longitudinal view of an exemplary adaptor employing the sensor-light/sound mechanism of FIG. 7.
Figure 9:
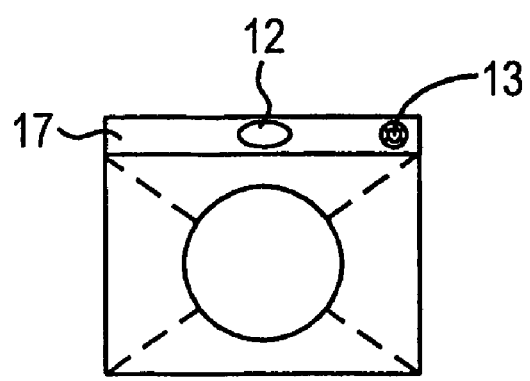
FIG. 9 is a frontal view of an exemplary adaptor with a sensor-light/sound mechanism according to the embodiment shown in FIG. 8.

A fourth embodiment of the instant invention is shown in FIG. 6 as adaptor 1C. As in the other embodiments, the fourth embodiment consists of a connecting side 2, a transition section 4, and a mouthpiece side 3. However, in the FIG. 6 embodiment, the transition section 4 comprises an elongate, curved, generally tubular section of constantly narrowing cross-section. The cross-sectional shape of the transition section 4 preferably is of airfoil shape, so as to minimize turbulence whereby to keep the aerated particles from colliding and coagulating. Further, the extension should be long enough to allow a care-giver to administer medicine from the inhaler to a person lying in a prone or semi-prone position, i.e., without the patient having to sit up or hold the inhaler. Finally, as in the other embodiments, the connecting means facilitates the immediate passage or medication between the inhaler mouthpiece and the oral contact means of the adaptor, without acting as a holding chamber for the medication.

In yet another embodiment of the present invention, illustrated in FIGS. 7-9, the mouthpiece adaptor or the MDI or DPI itself includes electronic means to teach the patient to retrieve a proper breathing pattern. Such electronic means includes a sensor 14, an on/off switch 15, a power source 16, actuation controller 17, noise or light generating means 18, a light 12, and optionally a speaker 13. As shown in FIG. 7, the actuation controller 17 supplies power to the noise and light generating means 18 only when the sensor 14 detects a patient is inhaling and the power switch 15 is on. Upon receiving power, the noise or light generating means 18 determines the strength and frequency of the inhalations, and generates light and sound based upon these values. If the patient is not attaining the proper breathing pattern for a particular device, the noise and light generating means 18 causes a light 12 to turn red, which signals to the patient to change his or her breathing pattern to conform to the protocols of the device. Correlating sounds may also be produced by the light/sound generating means 18 and output to the speaker 13. Once the proper breathing pattern is attained, the light 12 on the adaptor 1 changes from red to green, and/or the sound/light generating means 18 informs the patient that they have attained the proper breathing pattern.

In yet another embodiment of the present invention the electronic means to teach the patient to inhale properly is integral to the inhaler.

It will be appreciated that although the foregoing detailed description proceeded with reference being made to the preferred embodiments and methods of use, the present invention is not intended to be limited to these preferred embodiments and methods of use. Rather, the invention is of a broad scope and intended to be limited only as set forth in the accompanying claims.

What is claimed is:

1. A mouthpiece adaptor for a dry powder or metered dose inhaler from which charge bearing particles are delivered to a patient comprising:

a connecting side for connecting to a mouthpiece of an inhaler;

a mouthpiece side of reduced size relative to the inhaler mouthpiece; and a transition section between said connecting side and mouthpiece side, wherein the transition section is covered at least in part by a foil which is charged to the same charge as said particles, and the adaptor is smoothly tapered along its entire length from the connecting side to the mouthpiece side.

2. The adaptor of claim 1, further comprising attachment means for fixing the mouthpiece adaptor to the mouthpiece of an inhaler.

3. The adaptor of claim 2, wherein said attachment means comprises a clamp.

4. The adaptor of claim 3, wherein the mouthpiece side is round in cross-section.

5. The adaptor of claim 2, wherein the attachment means comprises a friction fit.

6. The adaptor of claim 2, wherein said attachment means comprises a rubber band.

7. The adaptor of claim 1, wherein the transition section is funnel shaped.

8. The adaptor of claim 1, wherein the transition section is curved.

9. The adaptor of claim 8, wherein said transition section is airfoil shaped, in part.

10. A mouthpiece adaptor for a dry powder or metered dose inhaler from which charge bearing particles are delivered to a patient comprising:

a connecting side for connecting to a mouthpiece of an inhaler;

a mouthpiece side of reduced size relative to the inhaler mouthpiece; and a transition section between said connecting side and mouthpiece side, wherein said adaptor includes a flow sensor, and is covered at least in part by a foil which is charged to the same charge as said particles.

11. The adaptor of claim 10, further comprising a noise generator operatively connected to said flow sensor.

12. The adaptor of claim 10, further comprising one or more lights operatively connected to said flow sensor.

13. A unitary mouthpiece adaptor for a dry powder or metered dose inhaler from which charge bearing particles are delivered to a patient comprising:

a connecting side for direct connection to a mouthpiece of an inhaler;

a mouthpiece side of reduced size relative to the inhaler mouthpiece; and a transition section between said connecting side and mouthpiece side, wherein the adaptor is smoothly tapered along its entire length to the mouthpiece side, and is covered at least in part by a foil which is charged to the same charge as the particles.

14. The adaptor of claim 13, further comprising attachment means for fixing the mouthpiece adaptor to the mouthpiece of an inhaler.

15. The adaptor of claim 14, wherein said attachment means comprises a clamp.

16. The adaptor of claim 15, wherein the mouthpiece side is round in cross-section.

17. The adaptor of claim 14, wherein the attachment means comprises a friction fit.

18. The adaptor of claim 13, wherein the transition section is funnel shaped.

19. A unitary mouthpiece adaptor for a dry powder or metered dose inhaler from which charge bearing particles are delivered to a patient comprising:
   a connecting side for direct connection to a mouthpiece of an inhaler;
   a mouthpiece side of reduced size relative to the inhaler mouthpiece; and
   a transition section between said connecting side and mouthpiece side,
   further comprising attachment means for fixing the mouthpiece adaptor to the mouthpiece of an inhaler,
   wherein said attachment means is a clamp, and
   wherein the transition section is covered, at least in part, by a foil which is charged to the same charge as the particles.

20. The adaptor of claim 19, wherein said attachment means comprises a rubber band.

21. The adaptor of claim 19, wherein the transition section is curved.

22. The adaptor of claim 21, wherein said transition section is airfoil shaped, in part.

23. A unitary mouthpiece adaptor for a dry powder or metered dose inhaler from which charge bearing particles are delivered to a patient comprising:
   a connecting side for direct connection to a mouthpiece of an inhaler;
   a mouthpiece side of reduced size relative to the inhaler mouthpiece; and
   a transition section between said connecting side and mouthpiece side,
   wherein said adaptor includes a flow sensor, and is covered at least in part by a foil which is charged to the same charge as the particles.

24. The adaptor of claim 23, further comprising a noise generator operatively connected to said flow sensor.

25. The adaptor of claim 23, further comprising one or more lights operatively connected to said flow sensor.

26. A mouthpiece adaptor for a dry powder or metered dose inhaler comprising:
   a connecting side for connecting to a mouthpiece of an inhaler;
   a mouthpiece side of reduced size relative to the inhaler mouthpiece; and
   a transition section between said connecting side and mouthpiece side,
   wherein said mouthpiece side has a cross-sectional size and shape of a drinking straw, and the adaptor is smoothly tapered along its entire length from the connecting side to the mouthpiece side whereupon airflow may be concentrated with minimum turbulence.

27. The adaptor of claim 26, further comprising attachment means for fixing the mouthpiece adaptor to the mouthpiece of an inhaler.

28. The adaptor of claim 26, wherein said attachment means comprises a clamp.

29. The adaptor of claim 27, wherein the attachment means comprises a friction fit.

30. The adaptor of claim 26, wherein the transition section is funnel shaped.

31. The adaptor of claim 27, wherein said attachment means comprises a rubber band.

32. The adaptor of claim 26, wherein the transition section is curved.

33. The adaptor of claim 26, wherein said transition section is airfoil shaped, in part.

34. A mouthpiece adaptor for a dry powder or metered dose inhaler comprising:
   a connecting side for connecting to a mouthpiece of an inhaler;
   a mouthpiece side of reduced size relative to the inhaler mouthpiece; and
   a transition section between said connecting side and mouthpiece side,
   wherein said mouthpiece side has a cross-sectional size and shape of a drinking straw, and the adaptor is smoothly tapered along its entire length from the connecting side to the mouthpiece side whereupon airflow may be concentrated with minimum turbulence, and
   wherein said adaptor further includes a flow sensor.

35. The adaptor of claim 34, further comprising a noise generator operatively connected to said flow sensor.

36. The adaptor of claim 34, further comprising one or more lights operatively connected to said flow sensor.

37. A unitary mouthpiece adaptor for a dry powder or metered dose inhaler comprising:
   a connecting side for direct connection to a mouthpiece of an inhaler;
   a mouthpiece side of reduced size relative to the inhaler mouthpiece; and
   a transition section between said connecting side and mouthpiece side,
   wherein the adaptor is smoothly tapered along its entire length to the mouthpiece side whereupon airflow may be concentrated with minimal turbulence, and
   wherein said mouthpiece side has a cross-sectional size and shape of a drinking straw.

38. The adaptor of claim 37, further comprising attachment means for fixing the mouthpiece adaptor to the mouthpiece of an inhaler.

39. The adaptor of claim 38, wherein said attachment means comprises a clamp.

40. The adaptor of claim 38, wherein the attachment means comprises a friction fit.

41. The adaptor of claim 37, wherein the transition section is funnel shaped.

42. A unitary mouthpiece adaptor for a dry powder or metered dose inhaler comprising:
   a connecting side for direct connection to a mouthpiece of an inhaler;
   a mouthpiece side of reduced size relative to the inhaler mouthpiece; and
   a transition section between said connecting side and mouthpiece side,
   further comprising attachment means for fixing the mouthpiece adaptor to the mouthpiece of an inhaler,
   wherein the adaptor is smoothly tapered along its entire length from the connecting side to the mouthpiece side whereupon airflow may be concentrated with minimum turbulence,
   wherein said attachment means comprises a clamp, and
   wherein said mouthpiece side has a cross-sectional size and shape of a drinking straw.

43. The adaptor of claim 42, wherein said clamp comprises a rubber band.

44. The adaptor of claim 42, wherein the transition section is curved.

45. The adaptor of claim 42, wherein said transition section is airfoil shaped, in part.

46. A unitary mouthpiece adaptor for a dry powder or metered dose inhaler comprising:

a connecting side for direct connection to a mouthpiece of an inhaler;

a mouthpiece side of reduced size relative to the inhaler mouthpiece; and a transition section between said connecting side and mouthpiece side, wherein said adaptor is smoothly tapered along its entire length from the connecting side to the mouthpiece side whereupon airflow may be concentrated with minimum turbulence, wherein said adaptor includes a flow sensor, and wherein said mouthpiece side has a cross-sectional size and shape of a drinking straw.

47. The adaptor of claim 46, further comprising a noise generator operatively connected to said flow sensor.

48. The adaptor of claim 46, further comprising one or more lights operatively connected to said flow sensor.

* * * * *